United States Patent [19]

Ranken et al.

[11] Patent Number: 4,727,148

[45] Date of Patent: * Feb. 23, 1988

[54] CERTAIN AROMATIZATION PROCESS FOR PREPARING 1-ALKYL-1,4-DIHYDRO-4-OXO-7-(4-PYRIDYL)-3-QUINOLINE CARBOXYLIC ACID

[75] Inventors: Paul F. Ranken; Venkataraman Ramachandran, both of Baton Rouge, La.

[73] Assignee: Ethyl Corporation, Richmond, Va.

[*] Notice: The portion of the term of this patent subsequent to Nov. 19, 2002 has been disclaimed.

[21] Appl. No.: 900,305

[22] Filed: Aug. 25, 1986

Related U.S. Application Data

[63] Continuation of Ser. No. 715,005, Mar. 22, 1985, Pat. No. 4,649,202, and a continuation-in-part of Ser. No. 511,831, Jul. 8, 1983, abandoned, and a continuation-in-part of Ser. No. 511,832, Jul. 8, 1983, abandoned, and a continuation-in-part of Ser. No. 511,913, Jul. 8, 1983, abandoned.

[51] Int. Cl.$^4$ ................. C07D 215/56; C07D 213/26
[52] U.S. Cl. ..................................... 546/156; 546/329; 546/346; 546/348
[58] Field of Search ....................... 546/156, 329, 346

[56] References Cited

U.S. PATENT DOCUMENTS

| | | | |
|---|---|---|---|
| 3,907,808 | 9/1975 | Lesher et al. | 546/156 |
| 4,118,557 | 12/1978 | Lesher | 546/268 |
| 4,405,792 | 9/1983 | Walter | 546/346 |
| 4,550,167 | 10/1985 | Ramachandran | 546/156 |
| 4,552,964 | 11/1985 | Ramachandran | 546/156 |
| 4,554,352 | 11/1985 | Ranken | 546/156 |

*Primary Examiner*—Alan L. Rotman
*Attorney, Agent, or Firm*—Donald L. Johnson; John F. Sieberth; Patricia J. Hogan

[57] ABSTRACT

A 4-cyclohexenylpyridine is brominatively aromatized to the corresponding 4-phenylpyridine by brominating the cyclohexenylpyridine, such as a 4-(halocyclohexenyl)pyridine, especially a 4-(4-halocyclohex-3-enyl)-pyridine hydrochloride, and heating the brominated product in the presence or absence of any added base or hydrogen acceptor to form, e.g., a 4-(halophenyl)pyridine. The invention is of particular utility in the manufacture of intermediates of antibacterial 1-alkyl-1,4-dihydro-4-oxo-7-(4-pyridyl)-3-quinolinearcarboxylic acids.

1 Claim, No Drawings

CERTAIN AROMATIZATION PROCESS FOR PREPARING 1-ALKYL-1,4-DIHYDRO-4-OXO-7-(4-PYRIDYL)-3-QUINOLINE CARBOXYLIC ACID

CROSS-REFERENCE TO RELATED APPLICATIONS

This application is a continuation of application Ser. No. 715,005, filed Mar. 22, 1985, now U.S. Pat. No. 4,649,202. This application is a continuation-in-part of copending applications Ser. Nos. 511,831, 511,832, and 511,913, all filed July 8, 1983, and now abandoned.

FIELD OF THE INVENTION

This invention relates to 4-phenylpyridines and more particularly to a process for preparing them by the aromatization of the corresponding cyclohexenylpyridines.

BACKGROUND

U.S. Pat. No. 4,405,792 (Walter I) discloses 4-(3-chlorocyclohex-3-enyl)pyridine, 4-(4-chlorocyclohex-3-enyl)pyridine, a process for making these compounds by a Diels-Alder reaction between chloroprene and a 4-vinylpyridine, and a process for converting them to 4-(3-chlorophenyl)pyridine and 4-(4-chlorophenyl)pyridine by catalytic dehydrogenation.

Copending application Ser. No. 495,977, filed May 19, 1983, in the name of Thomas J. Walter (Walter II), now U.S. Pat. No. 4,533,735, discloses processes by which 4-(4-halophenyl)pyridines, such as the 4-(4-chlorophenyl)pyridine produced in Walter I, can be converted to 4-(4-halo-3-nitrophenyl)pyridines, then to 4-(3-aminophenyl)pyridines, and ultimately to the antibacterial 1-alkyl-1,4-dihydro-4-oxo-7-pyridinyl-3-quinolinecarboxylic acids of Sterling Drug's U.S. Pat. Nos. 3,753,993 (Lesher et al.), 3,907,808 (Lesher and Catabateas), and 4,118,557 (Lesher).

Copending application Ser. No. 497,026, filed May 23, 1983, in the name of V. Ramachandran (Ramachandran I), now U.S. Pat. No. 4,552,963, discloses improved processes for preparing 4-(halocyclohex-3-enyl)pyridines and derivatives wherein a boron trifluoride catalyst is employed directly to improve the yield of 4-(4-halocyclohex-3-enyl)pyridine and indirectly to improve the yields of derivatives thereof.

Copending application Ser. No. 497,027, filed May 23, 1983, in the name of V. Ramachandran (Ramachandran II), now U.S. Pat. No. 4,550,167, discloses 4-(halocyclohex-3-enyl)pyridine salts which may be prepared by reacting 4-(halocyclohex-3-enyl)pyridines with relatively strong acids to facilitate isolating and/or aromatizing the 4-(halocyclohex-3-enyl)pyridines.

Separately and in combination, the aforementioned references disclose useful processes for preparing antibacterial agents and intermediates therefor. However, since the aromatization techniques taught in these references are not particularly efficient, there is still room for improvements in these processes. Also, it would be desirable to discover an aromatization technique that would not only permit the efficient aromatization of the difficulty aromatizable 4-(halocyclohex-3-enyl)pyridines of Walter and Ramachandran but also present an alternative method of aromatizing the more easily aromatizable 4-(cyclohex-3-enyl)pyridines having no halo substituents on the cyclohexene ring.

As described in March, *Advanced Organic Chemistry*, McGraw Hill (New York), 1977, pages 1077–1078, it is known that cyclohexenes can be aromatized in a variety of ways in addition to the ways taught by Walter and Ramachandran. However, it is also known that these other conventional techniques are sometimes unsatisfactory for the aromatization of particular cyclohexenes, and drastic conditions are occasionally required for the aromatization. For example, Newman et al., *Journal of the American Chemical Society*, Vol. 63, 1941, pp. 1542–1544, disclose the inadequacy of various aromatization techniques in attempted aromatizations of 3-methyl-1,2,3,6-tetrahydrophthalic anhydride.

Newman et al. teach that their 3-methyl-1,2,3,6-tetrahydrophthalic anhydride can be aromatized by heating it with bromine in acetic acid and pyrolyzing the bromine-containing intermediate thus obtained. It would be desirable to be able to modify this brominative aromatization to make it useful for the aromatization of cyclohexenylpyridines.

SUMMARY OF INVENTION

An object of this invention is to provide a novel process for preparing 4-phenylpyridines.

Another object is to provide such a process wherein the 4-phenylpyridines are prepared from 4-cyclohexenylpyridines.

Still another object is to aromatize cyclohexenylpyridines to phenylpyridines via novel intermediates.

A further object is to provide novel processes for preparing derivatives of 4-(halophenyl)pyridines.

These and other objects are attained by reacting a 4-cyclohexenylpyridine with at least one molar equivalent of a brominating agent at a temperature of about 20°–70° C. so as to add bromine to the double bond of the cyclohexene ring, heating the resultant brominated product at a temperature of about 80°–300° C. so as to form the corresponding 4-phenylpyridine, and, when appropriate, converting the 4-phenylpyridine to a desired derivative thereof.

DETAILED DESCRIPTION

Cyclohexenylpyridines that can be used in the brominative aromatization process of the invention are cyclohexenylpyridines which are unsubstituted or bear only innocuous substituents, i.e., substituents which do not interfere with the bromination, dehydrobromination, and dehydrogenation reactions that occur in the process—such innocuous substituents including, e.g., alkyl, carbalkoxy, and alkoxy groups containing 1–6 carbons, cyano, fluoro, chloro, bromo, etc. These cyclohexenylpyridines include both compounds that are easily aromatized by known techniques and compounds which have been at least difficult to aromatize in the past.

In a particularly interesting embodiment of the invention, the cyclohexenylpyridine is a 4-(halocyclohexenyl)pyridine, which may be any 4-(halocyclohexenyl)pyridine but is generally a 4-(4-halocyclohex-3-enyl)- or 4-(3-halocyclohex-3-enyl)pyridine or a hydrogen halide acid salt thereof. Such compounds, if desired, may have innocuous substituents on 1–4 of the free carbons of the pyridine ring, e.g., substituents such as fluoro; chloro; bromo; cyano; carboxyl; carbalkoxy; carbamyl; nitrogen-containing heterocyclic groups; substituted (e.g., halogenated) and unsubstituted alkyl, cycloalkyl, aralkyl, aryl, and alkaryl groups, optionally joined to the pyridine ring by an ether linkage; etc.. Any aliphatic groups in these substituents generally contain 1-6 carbons arranged in straight or branched chains.

The preferred 4-(halocyclohexenyl)pyridines are the hydrohalide salts, which are aromatized more easily than the free pyridines; and the 4-(4-chlorocyclohex-3-enyl)pyridine and 4-(3-chlorocyclohex-3-enyl)pyridine salts are especially preferred. When a product useful in preparing the aforementioned antibacterial agents is desired, the 4-(halocyclohexenyl)pyridine that is most preferred is 4-(4-chlorocyclohex-3-enyl)pyridine hydrochloride.

The 4-(halocyclohexenyl)pyridines may be prepared in any suitable manner, the preferred 4-(4-halocyclohex-3-enyl)pyridines and 4-(3-halocyclohex-3-enyl)pyridines being synthesizable, e.g., by the processes of Walter I, Ramachandran I, and Ramachandran II, the teachings of all of which are incorporated herein by reference.

The aforementioned 4-(halocyclohexenyl)pyridines are compounds which are difficult to aromatize by prior art techniques. Exemplary of the cyclohexenylpyridines which can be aromatized by known techniques but may desirably be aromatized by the process of the present invention instead of by the prior art techniques are 4-cyclohexenylpyridines, especially 4-(cyclohex-3-enyl)pyridines wherein the pyridine ring optionally bears 1-4 substituents such as those mentioned above and the cyclohexene ring optionally bears alkyl substituents containing 1-6 carbons in the 3- and/or 4-positions, as well as the hydrohalide salts of such compounds. Such compounds include, e.g., 4-(cyclohex-3-enyl)pyridine, 4-(4-alkylcyclohex-3-enyl)pyridines such as 4-(4-methyl-cyclohex-3-enyl)pyridine, 4-(3-methylcyclohex-3-enyl)pyridine, 4-(3,4-dimethyl-cyclohex-3-enyl)pyridine, etc., and are typically prepared by reacting a suitable diene, such as butadiene, isoprene, etc., with an appropriate dienophile, such as a substituted or unsubstituted 4-vinylpyridine, under conditions known to the art.

In the practice of the invention, the cyclohexenylpyridine is brominated in any convenient manner, suitably by reacting the cyclohexenylpyridine with at least one molar equivalent of a brominating agent, such as bromine, hydrogen bromide, N-bromosuccinimide, 1,3-dibromo-5,5-dimethylhydantoin, pyridinium bromide perbromide, etc., in an appropriate medium, such as acetic acid, chloroform, methylene chloride, etc., at a temperature of about 20°-70° C., preferably under reflux conditions, so as to add bromine to the double bond of the cyclohexene ring. There is no maximum amount of brominating agent that may be employed, but, as a practical matter, it is generally economically undesirable to use more than about 5 molar equivalents of the brominating agent, so it is most common to utilize about 1-2 molar equivalents of the brominating agent. The cyclohexenylpyridine that is brominated may be a substantially pure coumpound, or it may be a crude compound, such as the mixture of isomers that normally results from the Diels-Alder reactions of Walter I and Ramachandran I and II.

As indicated above, the bromination of the cyclohexenylpyridine sometimes leads to the formation of novel intermediates. These compounds may be generally described as 4-(3,4-dibromocyclohexyl)pyridines and include, e.g., 4-(3,4-dibromocyclohexyl)pyridine itself, 4-(3,4-dibromo-4-chlorocyclohexyl)pyridine, 4-(3,4-dibromo-4-methylcyclohexyl)pyridine, the hydrohalide salts thereof, and other 4-(3,4-dibromocyclohexyl)pyridines bearing one or two alkyl substituents, an additional halo substituent, or an alkyl substituent and an additional halo substituent in the 3- and 4-positions.

After completion of the bromination, which normally takes about 1-24 hours, e.g., in the case of the aforementioned 4-(halocyclohexenyl)pyridines, about 12-24 hours when a free pyridine is employed and a much shorter time, e.g., about 1-3 hours, when a pyridine hydrohalide is used, the brominated product is heated to dehydrohalogenate and dehydrogenate it in a single reaction and form a phenylpyridine. This step of the process is accomplished simply by heating the brominated product at about 80°-300° C., generally at about 100°-300° C., in the vapor or liquid phase, since the pyridine portion of the compound can serve both as the base and the hydrogen acceptor which would be expected to be required in such a reaction. However, if desired, the reaction may be conducted in the presence of an added base, such as sodium or potassium hydroxide or carbonate, a dialkyl or trialkylamine, etc., and in an inert solvent, such as diphenyl ether, etc.; or the reaction may be conducted in the presence of an added hydrogen acceptor, e.g., an olefin, such as hexene, dodecene, ethylene, styrene, etc.; a nitroalkane, such as nitroethane, 1-nitrohexane, 3-nitro-2,2-dimethylbutane, 2-nitro-2-methylpentane, etc.; a nitroarene, such as nitrobenzene, the 2-, 3-, and 4-nitrotoluenes, 2-nitro-1,3,5-trimethylbenzene, the 2- and 4-nitroethylbenzenes, etc. When the reaction is conducted in the presence of an added hydrogen acceptor, particularly preferred conditions are the use of nitrobenzene as the acceptor and the use of a reaction temperature of about 100°-200° C., e.g., about 160° C.

When derivatives of the phenylpyridines are to be prepared, they are generally synthesized from the phenylpyridines by conventional techniques. For example, when derivatives of the 4-(halophenyl)pyridines are desired, they may be formed by subjecting the 4-(4-halophenyl)pyridines to the appropriate reactions, e.g., the reactions taught in Walter II, the teachings of which are incorporated herein by reference.

When the processes of Walter II are to be used, the object is generally to form derivatives of a 4-(4-halophenyl)pyridine, which is sometimes prepared in admixture with a 4-(3-halophenyl)pyridine. In such a situation, it may be desirable first to separate the desired starting material from any isomer with which it is in admixture. However, if desired, a crude starting material, e.g., a 4-(4-halophenyl)pyridine containing a 4-(3-halophenyl)pyridine impurity, may be employed in these processes.

In general, when one or more of the processes of Walter II are to be employed, a 4-(4-halophenyl)pyridine—alone or in admixture with a 4-(3-halophenyl)pyridine—is nitrated to a 4-(4-halo-3-nitrophenyl)pyridine, preferably 4-(4-chloro-3-nitrophenyl)pyridine, which may then be reduced to a 4-(3-aminophenyl)pyridine, such as 4-(3-aminophenyl)pyridine itself. Then, when antibacterial agents, such as the 1-alkyl-1,4-dihydro-4-oxo-7-pyridinyl-3-quinolinecarboxylic acids of Lesher, Lesher et al., and Lesher and Carabateas are desired, they—or their intermediates—may be prepared by subjecting the 4-(3-aminophenyl)pyridines to suitable reactions which may be conducted by known techniques.

For example:

(1) the 4-(3-aminophenyl)pyridine may be reacted with a dialkyl ethoxymethylenemalonate to form a dialkyl 3-(4-pyridyl)anilinomethylenemalonate, which may be cyclized to an alkyl 1,4-dihydro-4-oxo-7-(4-pyridyl)-3-quinolinecarboxylate, which in turn may be N-alkylated to an alkyl 1-alkyl-1,4-dihydro-4-oxo-7-(4-pyridyl)-3-quinolinecarboxylate, which may then be hydrolyzed to the corresponding acid, as in Lesher et al. and Lesher and Carabateas, (2) the 4-(3-aminophenyl)pyridine may be reductively alkylated, or it may be acylated and then reduced, as in Lesher, to form a 4-(3-alkylaminophenyl)pyridine, otherwise designated as a 3-(4-pyridyl)-N-alkylaniline, which may then be (a) subjected to the reaction steps of Lesher et al. and Lesher and Carabateas without the need for their N-alkylation step or (b) subjected to reaction with a cyclic alkylidenyl alkoxymethylenemalonate, etc., as in Lesher, to form the antibacterial agent, or (3) either of the above procedures may be terminated at the end of any step to recover a desired product for use in any other desired process, etc.

As in Walter II, when an acylated 4-(3-aminophenyl)pyridine is desired, it is sometimes convenient to combine the reduction and acylation steps, e.g., by reducing the 4-(4-halo-3-nitrophenyl)pyridine with hydrogen in the presence of sodium acetate, a palladium-on-carbon catalyst, and glacial acetic acid—a process which leads to a high yield of 4-(3-aminophenyl)pyridine at 60°–70° C. but which produces substantial yields of 4-(3-acetamidophenyl)pyridine when conducted for a sufficient time at temperatures near 80° C. Alternatively and more efficiently, 4-(3-acetamidophenyl)pyridine can be produced by including acetic anhydride in the reduction recipe.

The following examples are given to illustrate the invention and are not intended as a limitation thereof.

EXAMPLE I

A suitable reaction vessel was charged with 318 mg (2 mmols) of 4-(cyclohex-3-enyl)pyridine and 20 ml of carbon tetrachloride, to which was added 340 mg (2 mmols) of 48% reagent HBr. Then 392 mg (2.2 mmols) of N-bromosuccinimide and 50 mg (0.2 mmol) of benzoyl peroxide were added, and the reaction mixture was refluxed. After about 30 minutes of refluxing, the reaction mixture was cooled to ambient temperature. The carbon tetrachloride was decanted off and removed on an aspirator to isolate 250 mg of a solid which was recrystallized from n-hexane to provide 70 mg of 4-(3,4-dibromocyclohexyl)pyridine, a white solid having a melting point of 75°–77° C. Heating of this dibromide at 200°–300° C. resulted in a substantial conversion to 4-phenylpyridine and 4-(cyclohex-3-enyl)pyridine, which analysis showed to be in an area ratio of 2.2/1.

EXAMPLE II

A suitable reaction vessel was charged with 340 mg of a mixture of 70 mol % of 4-(4-chlorocyclohex-3-enyl)pyridine and 30 mol % of 4-(3-chlorocyclohex-3-enyl)pyridine, 310 mg of bromine, and 10 ml of methylene chloride and stirred at room temperature overnight. The methylene chloride was then removed by evaporation and nmr revealed that no starting material remained in the product left behind.

A mixture of the crude bromination product, 340 mg of anhydrous potassium carbonate, and 10 ml of diphenyl ether was slowly heated to about 240° C. After two hours, the reaction mixture was cooled and reheated to resolubilize crystalline material.

The crude reaction mixture was taken up in diethyl ether and extracted with 1N HCl, after which the acid layer was washed, neutralized, and extracted with methylene chloride to give about 400 mg of crude reaction product. Analysis of this product after drying, filtration, and evaporation showed that the reaction resulted in the production of approximately equal amounts of phenylpyridine and chlorophenylpyridine.

EXAMPLE III

A suitable reaction vessel was charged with 0.5 g of a mixture of 70 mol % of 4-(4-chlorocyclohex-3-enyl)pyridine and 30 mol % of 4-(3-chlorocyclohex-3-enyl)pyridine, 0.5 g of bromine, and methylene chloride and stirred at room temperature overnight. The excess bromine and methylene chloride were then removed by evaporation. The product was then heated for 8 hours at 115° C. in 5 ml of nitrobenzene to form a crude reaction mixture, which was partitioned between diethyl ether and 1N HCl, extracted with 1N HCl, washed, neutralized, extracted with methylene chloride, dried, filtered, and evaporated to isolate a product which was analyzed and determined to contain 65–75% 4-(4-chlorophenyl)pyridine.

EXAMPLE IV

A solution of 1 g of 4-(4-chlorocyclohex-3-enyl)pyridine hydrochloride in 20 ml of chloroform was refluxed for two hours with one molar equivalent of bromine. Then the chloroform was removed, 10 ml of a 50:50 mixture of nitrobenzene and diphenyl ether was added, and the reaction mixture was heated to 125° C. for one hour. After being worked up, the crude reaction mixture was analyzed by nmr and determined to contain 4-(4-chlorophenyl)pyridine and starting material in a 2/1 ratio.

EXAMPLE V

A solution of 5 g of 4-(4-chlorocyclohex-3-enyl)pyridine hydrochloride in 40 ml of chloroform was refluxed for one hour with 1.1 molar equivalents of bromine. At the end of the hour, 25 ml of the chloroform was distilled off, and the remaining solution was refluxed for another hour. Then the excess chloroform was removed, 40 ml of nitrobenzene were added, and the mixture was heated to 170° C. and kept there for four hours with a slow stream of nitrogen flowing over it. After being worked up, the crude reaction product was analyzed by nmr and accordingly estimated to contain about 86% of 4-(4-chlorophenyl)pyridine.

It is obvious that many variations may be made in the products and processes set forth above without departing from the spirit and scope of this invention.

We claim:

1. In a process for preparing a 1-alkyl-1,4-dihydro-4-oxo-7-(4-pyridyl)-3-quinolinecarboxylic acid by (a) reacting a haloprene with a 4-vinylpyridine to form a 4-(4-halocyclohex-3-enyl)pyridine, (b) reacting the 4-(4-halocyclohex-3-enyl)pyridine with hydrochloric acid to form a hydrochloride, (c) aromatizing the resultant 4-(4-halocyclohex-3-enyl)pyridine hydrochloride to a 4-(4-halophenyl)pyridine, (d) nitrating the 4-(4-halophenyl)pyridine, (e) reducing the resultant 4-(4-halo-3-nitrophenyl)pyridine to a 4-(3-aminophenyl)pyridine, (f) converting the 4-(3-aminophenyl)pyridine to an alkyl 1-alkyl-1,4-dihydro-4-oxo-7-(4-pyridyl)-3-quinolinecarboxylate, and (g) hydrolyzing the resultant ester, the improvement which comprises aromatizing the 4-(4-halocyclohex-3-enyl)pyridine hydrochloride by reacting it with 1-5 molar equivalents of a brominating agent at a temperature of 20°–70° C. to add bromine to the double bond of the cyclohexene ring and heating the resultant brominated product at a temperature of 80°–300° C. to form the 4-(4-halophenyl)pyridine.

* * * * *